United States Patent
Taft

(10) Patent No.: US 9,668,965 B2
(45) Date of Patent: *Jun. 6, 2017

(54) TOPICAL COMPOSITION FOR TREATMENT OF SKIN, HAIR, AND/OR NAILS AND METHOD OF USING THE SAME

(71) Applicant: Hummingbird Industires, North Haledon, NJ (US)

(72) Inventor: Camilla A Taft, North Haledon, NJ (US)

(73) Assignee: Hummingbird Industries, North Haledon, NJ (US)

( * ) Notice: Subject to any disclaimer, the term of this patent is extended or adjusted under 35 U.S.C. 154(b) by 198 days.

This patent is subject to a terminal disclaimer.

(21) Appl. No.: 14/628,769

(22) Filed: Feb. 23, 2015

(65) Prior Publication Data

US 2015/0164782 A1   Jun. 18, 2015

Related U.S. Application Data

(63) Continuation-in-part of application No. 14/470,246, filed on Aug. 27, 2014, now Pat. No. 9,446,082.

(60) Provisional application No. 61/959,559, filed on Aug. 27, 2013.

(51) Int. Cl.

| | | |
|---|---|---|
| A61K 36/00 | (2006.01) |
| A61K 36/02 | (2006.01) |
| A61K 8/97 | (2017.01) |
| A61Q 5/00 | (2006.01) |
| A61Q 19/00 | (2006.01) |
| A61K 8/66 | (2006.01) |
| A61K 9/00 | (2006.01) |
| A61K 47/12 | (2006.01) |
| A61K 47/26 | (2006.01) |
| A61K 47/42 | (2017.01) |
| A61K 36/03 | (2006.01) |
| A61K 36/05 | (2006.01) |
| A61Q 19/08 | (2006.01) |
| A61Q 3/00 | (2006.01) |

(52) U.S. Cl.
CPC .............. *A61K 8/975* (2013.01); *A61K 8/66* (2013.01); *A61K 9/0014* (2013.01); *A61K 36/03* (2013.01); *A61K 36/05* (2013.01); *A61K 47/12* (2013.01); *A61K 47/26* (2013.01); *A61K 47/42* (2013.01); *A61Q 5/002* (2013.01); *A61Q 19/00* (2013.01); *A61Q 19/08* (2013.01); *A61K 2800/522* (2013.01); *A61Q 3/00* (2013.01)

(58) Field of Classification Search
None
See application file for complete search history.

(56) References Cited

FOREIGN PATENT DOCUMENTS

JP   2000072642 A   3/2000

OTHER PUBLICATIONS

Thomas et al. (1994) Infection and Immunity, Feb., p. 529-535.*
Shin, et al; Antibacterial Activity of the Lactoperoxidase System Combined with Edible Laminaria Hot-Water Extract as a Source of Halide Ions; Biosci. Biotechnol. Biochem, 76, (2) 404-406, 2012.
Product literature Dermikelp Cream 2011 http://www.africanbotanicals.com/All-Products/c166/p399/Dermikelp-Cream-50ml/product_info.html.
Product Literature Dermikelp Shampoo http://www.africanbotanicals.com/All-Products/c166/p401/Dermikelp-Shampoo/product_info.html.
Product Literature Dermikelp Cream 2015 http://www.iheal.co.za/products.html?page=shop.product_details&flypage=flypage. tpl&product_id=2819&category_id=145.
Product information Ecklon Home Page 2015 http://www.ecklon.net/.
Product information Ecklon General Information Page 2015 http://www.ecklon.net/information.htm.
Ecklon Algae Cleansing Bar Product Information 2015 http://www.ecklon.net/products_1.htm.
Ecklon Marine Exfoliating Scrub Product Information 2015 http://www.ecklon.net/products_2.htm.
Ecklon Marine Exfoliating Body Gel Product Information 2015 http://www.ecklon.net/products_11.htm.
Ecklon Intensive Anti-Cellulite and Slimming Gel Product Information 2015 http://www.ecklon.net/products_6.htm.
Ecklon Advanced Body Lotion Product Information 2015 http://www.ecklon.net/products_7.htm.
Ocean Glow Rejuvenating Hair and Body Mist; the Cuttingedge catalog; http://www.cutcat.com/item/Ocean_Glow_Hair_Body_Mist/440; web page accessed Oct. 25, 2016; copyrighted 2007.
Ocean Glow Rejuvenating Hair and Body Mist; Knutson Harvest catalog; http://knutsonsharvest.com/cambrian-OceanGlow-catalog.html; 4 pages, undated; web page accessed Oct. 25, 2016.

\* cited by examiner

*Primary Examiner* — Chris R Tate
*Assistant Examiner* — Russell Fiebig
(74) *Attorney, Agent, or Firm* — Irving M. Fishman

(57) ABSTRACT

A topical composition includes an amount of a concentrate derived from *Ecklonia maxima* (sea kelp) effective for treating the skin, hair and/or nails and a dermatologically acceptable carrier.

23 Claims, 1 Drawing Sheet

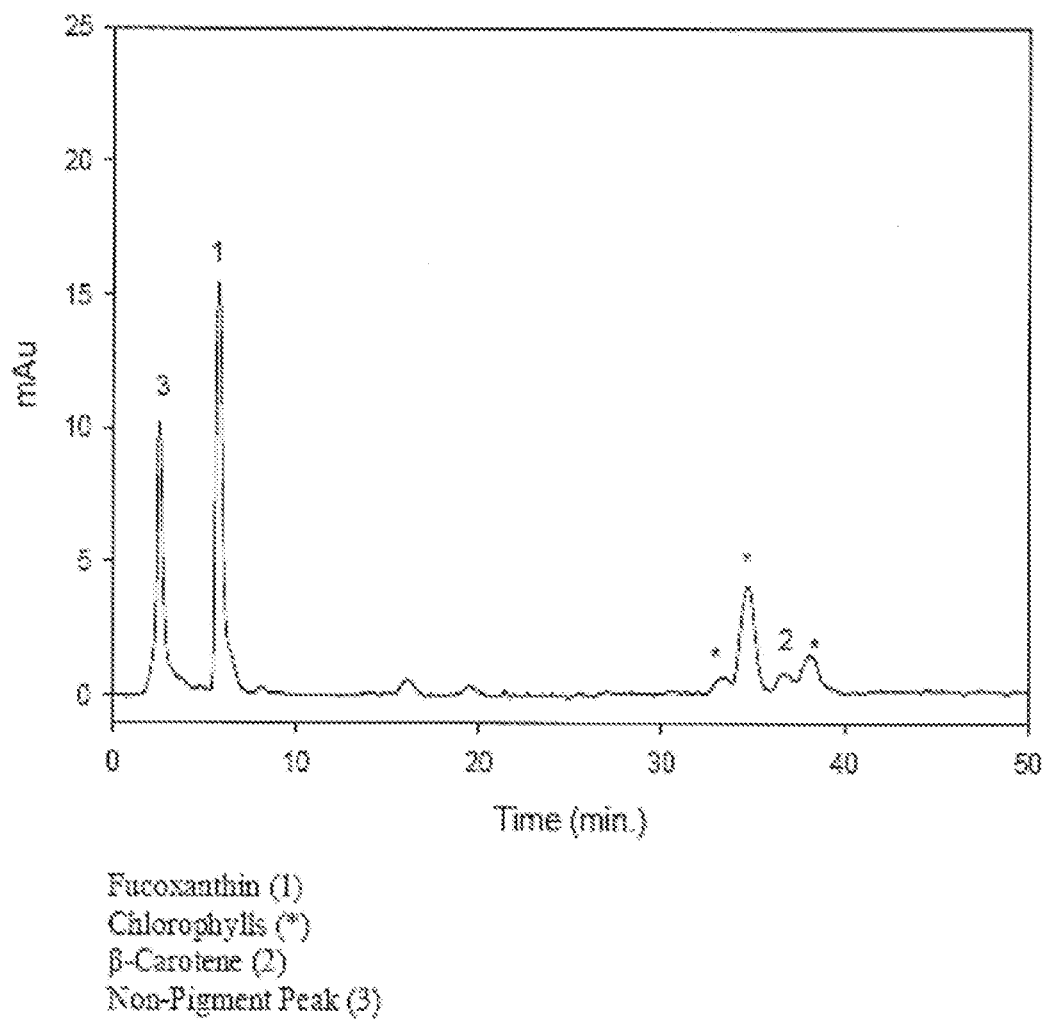

TOPICAL COMPOSITION FOR TREATMENT OF SKIN, HAIR, AND/OR NAILS AND METHOD OF USING THE SAME

CROSS-REFERENCE TO RELATED APPLICATIONS

The present application is a continuation-in-part of co-pending U.S. application Ser. No. 14/470,246, filed Aug. 27, 2014, which is a non-provisional application corresponding to and claiming benefit of U.S. Provisional Application Ser. No. 61/959,559, filed Aug. 27 2013.

FIELD OF THE INVENTION

The present invention relates to topical compositions, and more particularly, a topical composition for treatment of skin, hair and/or nails and method of using the same.

BACKGROUND OF THE INVENTION

Over time, exposure to certain environmental factors such as, for example, excess sunlight, dry air, pollutants, and abrasives, can adversely affect the skin, hair and/or nails. These effects can lead to conditions that are generally considered visually and physiologically undesirable.

Accordingly, there is a need for a topical composition formulated to treat skin, hair, and/or nails afflicted with a condition in need of treatment. There is also a need for a topical composition with an enhanced shelf-life containing actives that are effective and/or aid in preventing damage associated with aging and environmental stresses, improve visual appearance and promote healing of the skin, hair and/or nails. There is a further need for a topical composition that is safe, relatively easy to make and apply to the afflicted skin, hair and/or nails.

SUMMARY OF THE INVENTION

The present invention relates generally to a topical composition formulated to treat skin, hair, and/or nails afflicted with a condition in need of treatment, and a method of using the same. The condition may be the result of aging and/or other damage in the skin, hair and/or nails due to environmental effects or stresses. The present invention is especially suitable for use in skin, hair and/or nails treatment applications. The present invention is specifically formulated to prevent or protect the skin, hair and/or nails against such conditions, improve visual appearance and texture, and promote healing. In particular, the topical composition of the present invention includes a concentrate derived from *Ecklonia lonia maxima* (sea bamboo hereinafter 'sea kelp') providing a combination of bioactive components such as, for example, organic gels, vitamins, amino acids, enzymes, phenolic compounds and minerals, in combination with a dermatologically acceptable carrier.

In one aspect of the present invention, there is provided a topical composition comprising:
an amount of a concentrate derived from *Ecklonia maxima* (sea kelp) effective for treating the skin, hair and/or nails; and
a dermatologically acceptable carrier.

In another aspect of the present invention, there is provided a method of treating skin, hair and/or nails afflicted with a condition in need of treatment, comprising topically applying the topical composition described above to the skin, hair and/or nails afflicted with the condition.

DETAILED DESCRIPTION OF THE INVENTION

The present invention is directed to a topical composition formulated to treat skin, hair, and/or nails afflicted with a condition in need of treatment, and a method of using the same. The condition may be the result of aging and/or other damage in the skin, hair and nails due to environmental effects or stresses. The present invention is especially suitable for use in skin, hair and/or nails treatment applications. The present invention is specifically formulated to prevent or protect the skin, hair and/or nails against such conditions, improve visual appearance and texture, and promote healing. In particular, the topical composition of the present invention includes a concentrate derived from *Ecklonia maxima* (sea kelp) providing a combination of bioactive components such as, for example, organic gels, vitamins, amino acids, enzymes, phenolic compounds and minerals, in combination with a dermatologically acceptable carrier.

The present invention alleviates conditions including, but not limited to, burns; skin irritations such as those resulting from waxing, from laser treatments, from tattooing sessions, from bug bites, fungal infections (such as without limitation athlete's foot), itching and irritation such as those resulting from, without limitation, poison ivy, poison oak, poison sumac, and nettles, and other contact dermatitis reactions from rashes, from razor burns, from shingles, from eczema, from hyperpigmentation, from hives, from scarring, from psoriasis, from dry and cracked skin, from dry brittle hair and/or brittle nails, from dandruff, from itchy scalp, and the like, or combinations thereof.

In one embodiment of the present invention, there is provided a topical composition comprising an amount of a primary or secondary concentrate (the secondary concentrate being the primary concentrate diluted with water to a solids concentration as set forth below) derived from *Ecklonia maxima* (sea kelp) effective for treating the skin, hair and/or nails, and a dermatologically acceptable carrier. The present topical composition is formulated to work at the cellular level to repair, promote skin, hair and/or nail health. In a further embodiment of the present invention, the amount of the *Ecklonia maxima* primary or secondary concentrate, preferably secondary concentrate, is in the range of from about 0.1 wt % to 99 wt % based on the total weight of the composition, preferably from about 10 wt % to 60 wt %, and more preferably at about 33.3 wt %.

*Ecklonia maxima* is a species of kelp native to the southern oceans, and is most typically found off the coast of the western tip of Africa. *Ecklonia maxima* is composed of a strong and rubbery cell structure which enables it to thrive in the violent wave action present on this coastal area. The strength of this marine kelp is due to the presence of high levels of organic gels within its tissue. In addition to organic gels, the kelp possesses significant amounts of vitamins, minerals, enzymes, phenolic compounds and amino acids. In the present invention, the primary and secondary concentrates of *Ecklonia maxima* contain high levels of cytoplasm and alginate, and are obtained from freshly harvested *Ecklonia* kelp via mechanical cell burst processing. This processing involves mechanical cell disruption, and avoids chemical cell disruption, cell disruption by irradiation, cell disruption by drying and cell disruption by other techniques that can diminish or destroy the actives in the concentrate.

The *Ecklonia maxima* can be sourced through any of the South African government approved kelp sources. The raw kelp is then mechanically disrupted to provide a source of primary concentrate material. The primary concentrate material can be used if desired, but it is preferable to dilute the primary concentrate to the secondary concentrate with sufficient water to result in a solids concentration of from about 0.1 wt % to about 99 wt % solids content, preferably about 10 wt % to about 60 wt %, more preferably about 20 wt % to about 50 wt %, still more preferably about 30 wt % to about 40 wt %, most preferably about 33.3 wt % solids content.

The actives of the present invention when applied to the skin, hair and/or nails forms a protective coating or membrane that provides skin benefits including, but not limited to, moisturization, hydration, re-hydration, nutritive delivery, skin texture enhancement, scar reduction or removal, wound healing promotion, hyperpigmentation relief, ultraviolet type A and type B protection, skin soothing relief from conditions causing irritation due especially to sun burn, waxing, bug bites, athlete's foot, poison ivy, poison oak, poison sumac and nettles, rash, razor burn, shingles, eczema, psoriasis, hives, cracked skin, and the like; and that provides hair and/or nails benefits including, but not limited to, improved softness, improved manageability, improved luster and shine, improved thickness, improved moisturization and/or conditioning, improved color retention for color treated hair, hot iron damage relief, dandruff relief, itchy scalp relief, chemical treatment repair, damaged or dry nail cuticle repair, and the like.

The topical composition includes any suitable dermatologically acceptable carrier selected from wet-wipe delivery, aerosols, emulsion, liquid, foam, dispersions, creams, gels, pastes, ointments, sprays, serums, lotions, shampoos, bars, salves, and the like that are compatible with the active materials in the sea kelp concentrate used herein. In a preferred embodiment of the present invention, the topical composition is in the form of a serum spray. In a preferred embodiment of the present invention, the dermatologically acceptable carrier is deionized water. The dermatologically acceptable carrier may be present in an amount of from about 10 wt % to about 99 wt % based on the total weight of the composition, and preferably from about 20 wt % to about 80 wt %, and more preferably at about 64.34 wt %.

The topical composition may also include other optional ingredients including, but not limited to, pH adjusters, buffers, thickening agents, preservatives, colorants, pigments, fillers, opacifiers and perfumes. Non-limiting further optional ingredients include those listed in:

(a) The Honest Company Wipes, such as:
Purified Water, Citric Acid (Fruit-Based Stability Agent), Silver Dihydrogen Citrate (All Natural, Water-Soluble Preservative), Decyl Glucoside (Sugar-Based Cleanser), Sodium Citrate (Corn-Based Antioxidant), *Punica Granatum* (Pomegranate Fruit) Extract, *Glycyrrhiza Uralensis* (Licorice Root) Extract, *Chamomilla Recutita* (Chamomile) Extract, *Cucumis Sativus* (Cucumber Fruit) Extract, *Peucedanum Ostruthium* (Masterwort Leaf) Extract (b) The Honest Company Sunscreen, such as:
Non-Nano Titanium Dioxide 7.8% (Mineral Sunscreen), Alumina, Bentonite, Butyloctyl Salicylate, Caprylhydroxamic Acid, Caprylyl Glycol, *Carthamus Tinctorius* (Safflower) Seed Oil, Cetearyl Alcohol, Coco Glucoside, Ethylhexylglycerin, Glycerin, Heptyl Undecylenate, Hydrogenated Methyl Abietate, Silica, Water (c) The Honest Company Shave oil and After Shave, such as:
*Helianthus Annuus* (Sunflower) Seed Oil*, *Ricinus Communis* (Castor) Seed Oil*, *Vitis Vinifera* (Grapeseed) Oil*, *Sesamum Indicum* (Sesame) Seed Oil*, *Argania Spinosa* (Argan) Oil*, *Calendula Officinalis* Flower Oil*, *Rosa Canina* (Rosehip) Seed Oil*, *Macadamia Ternifolia* (Macadamia Nut) Oil*, *Lavandula Angustifolia* (Lavender) Oil*, *Citrus Bergamia* (Bergamot) Oil*, *Salvia Sclarea* (Clary Sage) Oil*, Menthol Crystals*, *Melaleuca Alternifola* (Tea Tree) Oil*, *Rosmarinus Officinalis* (Rosemary) Oil*, *Simmondsia Chinensis* (Jojoba) Seed Oil*, *Aloe Barbadensis* (*Aloe*) Vera Leaf Juice*, Tocopherol (Non-GMO), *Calophyllum Inophyllum* (Tamanu) Oil (d) Burt's Bees Carrot Seed Oil Complexion Mist for Dry Skin, such as
Purified water, rose oil, sandlewood oil, balsam peru, carrot seed oil, vetiver oil (e) Mario Badescu Facial Spray with *Aloe*, Herbs & Rosewater, such as:
Deionized water, *Aloe* Vera Gel, Bladdarwrack Extract, Herbal Extract, Rose Extract, *Gardenia* Extract, Propylene Glycol (f) MAC Fix+, such as:
Water, Glycerin, Butylene Glycol, *Cucumis Sativus* (Cucumber) Fruit Extract, *Chamomilla Recutita* (Matricaria) Extract, *Camellia Sinensis* Leaf Extract, Tocopheryl Acetate, Caffeine, Panthenol, Arginine, PEG-40 Hydrogenated Castor Oil. PPG-26-Buteth-26, Fragrance, Disodium EDTA, Phenoxyethanol (g) Evian Facial Water Spray, such as:
Minerals, including, but not limited to, calcium (about 80 mg/ml), chloride (about 6.8 mg/ml), bicarbonate (about 360 mg/ml), magnesium (about 26 mg/ml), nitrate (about 3.7 mg/ml), potassium (about 1 mg/ml), silica (about 15 mg/ml), sodium (about 6.5 mg/ml), sulfates (about 12/6 mg/ml) (the concentrations mentioned with respect to each being an exemplary non-limiting amount)

(h) Perricone MD Neuropeptide Firming Moisturizer, such as:
Water, Isopropyl Palmitate, Taurine, Cetearyl Alcohol, L-Tyrosine, Phosphatidylcholine, Ceteareth-20, Glyceryl Stearate, PEG-100 Stearate, Dimethyl MEA (DMAE), Dimethicone, Phenoxyethanol, Caprylyl Glycol, Pyridoxine HCl, Disodium EDTA, *Elaeis Guineensis* (Palm) Oil, Tocotrienols, Sorbic Acid, Tocopherol, Sodium Hyaluronate, Acetyl Hexapeptide-8 (Neuropeptide), Fragrance (i) La Mer Moisturizing Crème, such as:
Seaweed (Algae) Extract, Mineral oil Glycerin, Isohexadecane, *Citrus Aurantifolia* (Lime) Extract, Microcrystalline Wax, Lanolin Alcohol, Sesame Seed Oil, *Eucalyptus* Oil, Magnesium Sulfate, Sesame Seed, *Medicago sativa* (alfalfa) seed powder, *Helianthus Annuus* (sunflower) Seedcake, *Prunus amygdulus dulcis* (sweet almond) seed meal, Sodium Gluconate, Potassium Gluconate, Copper Gluconate, Calcium Gluconate, Magnesium Gluconate, Zinc Gluconate, Paraffin, Tocopheryl succinate, Niacin, Beta-carotene, Decyl oleate, Aluminium distearate, Octyldodecanol, Citric acid, Cyanocobalamin, Magnesium stearate, Panthenol, Limonene, Geraniol, Linalool, Hydroxycitronellal, Citronellol, Benzyl salicylate, Citral, Methylchloroisothiazolinone, Methylisothiazolinone, Alcohol Denat., Fragrance (Parfum)

(j) Ocean Glow Nourishing Hair and Body Mist, such as: Pocono Mountain Water 67%, *Ecklonia Maxima* kelp cytoplasm 33%, Organically Certified Essential Oils 0.14% a combination of rosemary and lavender oils, Organic Stabilizers a combination of Acetic Acid and Hydrogen Peroxide levels below 0.1%.

The present invention further includes components especially useful in enhancing the shelf life of the actives present in the topical composition. In particular, the topical composition further includes a shelf life enhancer for maintaining the actives contained therein at optimal efficacy levels for an extended period of time as compared to compositions absent such enhancers. In a preferred embodiment of the present invention, the shelf life enhancer includes an antimicrobial effect.

In one embodiment of the present invention, the effective amount of the shelf life enhancer present in the topical composition is up to 40 wt % based on the total weight of the composition, preferably from about 0.001 wt/o to 30 wt % and more preferably from about 0.1 wt % to 20 wt %.

In a preferred embodiment of the present invention, the shelf life enhancer comprises an enzyme component and a substrate component. The enzyme component may be preferably selected from a peroxidase, an oxidase or combinations thereof, and the substrate component may be preferably selected from glucose, iodide, thiocyanate, or combinations thereof, which are catalytically compatible with at least one of the enzymes present in the topical composition.

In a further preferred embodiment of the present invention, the enzyme component is present in an amount of at least 0.001 wt % based on the total weight of the composition, preferably from about 0.025 wt % to 1 wt %, and more preferably at about 0.05 wt %, and the substrate component is present in an amount of at least 0.001 wt % based on the total weight of the composition, preferably from about 0.5 wt % to 10 wt %, and more preferably at about 1.0 wt %. In a further embodiment of the present invention, the weight ratio of the substrate component to enzyme component is at least 2:1, preferably from about 5:1 to 100:1, and more preferably at about 20:1.

In a further embodiment of the invention, the present composition includes a buffer to maintain a pH value in the range of from about 4 to 7, preferably 4.2 to 6.5, more preferably 4.9 to 5.1. This can be achieved by incorporating a buffer system such as, for example, without limitation, citric acid and citrate. The buffer may be present in an amount of from about 1 wt. % to 2 wt % based on the total weight of the composition. The addition of a buffer system minimizes downward drift of pH that may undesirably occur during storage and transport.

In a more preferred embodiment of the present invention, the topical composition includes an enzyme component comprising a peroxidase selected from lactoperoxidase, an oxidase selected from glucose oxidase, in combination with a substrate component comprising glucose (more preferably glucose in combination with iodide and thiocyanate).

In another embodiment of the present invention, there is provided a method of treating skin, hair and/or nails afflicted with a condition in need of treatment, comprising topically applying the topical composition of the present invention to the skin, hair and/or nails afflicted with the condition. The topical composition is applied in an effective amount sufficient to alleviate the condition for a given treatment regimen. The present topical composition may be topically applied to exposed areas of the body as needed.

During application, a small quantity of the topical composition, for example, from about 1 mL to 100 mL, may be applied to exposed areas of the body, from a suitable container or applicator, and if necessary, it is then spread over and/or rubbed into the skin, hair and/or nails using the fingers or hand or a suitable delivery apparatus. The application can be made through spraying or a wet-wipe delivery system.

Alternatively, application of the composition may be had through use of a 'wipe' which has been saturated with the appropriate composition of the invention and enclosed in a sealed or re-sealable container until ready for use. Individual pouches similar to those used for alcohol swabs are suitable containers for such wipes, as are multiple use wipe containers such as those used for baby wipes, such as those used for Neutrogena face cleansing wipes, such as those used for Clorox Cleansing wipes.

Additional products of the invention can be achieved by adding the primary or secondary concentrate and optionally adding the aforementioned shelf-life enhancer component in the stated concentrations to a host of commercially available products used in the cosmetic and topical pharmaceutical fields for the treatment of hair, skin, or nails. Representative products available as of July 2013 (to which the kelp concentrates and optionally the shelf life extender can be added) include, without limitation, the aforementioned commercially available products (a) through (i)
  (a) The Honest Company Wipes, www.honest.com,
  (b) The Honest Company Sunscreen, www.honest.com
  (c) The Honest Company Shave oil and After Shave, www.honest.com
  (d) Burt's Bees Carrot Seed Oil Complexion Mist for Dry Skin,
  (e) Mario Badescu Facial Spray with *Aloe*, Herbs & Rosewater,
  (f) MAC Fix+,
  (g) Evian Facial Water Spray,
  (h) Perricone MD Neuropeptide Firming Moisturizer,
  (i) La Mer Moisturizing Crème
  (j) Ocean Glow Nourishing Hair and Body Mist and further the following non-limiting additional products:
all the specific components of which are hereby incorporated by reference as components for use in the present invention. Where the shelf life extender of the present invention mentioned above is the enzyme components mentioned hereinabove together with the glucose. Iodide, thiocyante substrate component mentioned above, cationic surfactants are preferably avoided, as they can interfere with the workings of the enzyme/substrate reaction. However, no such restriction is imposed where the enzyme components mentioned hereinabove together with the glucose. Iodide, thiocycante substrate component mentioned above are not present. In most of the commercial products mentioned in this paragraph, preservatives and antibacterials, etc are present in sufficient amounts that the hereinbefore mentioned enzyme component and glucose, iodide, thiocyanate substrate component do not need to be present for suitable shelf life, but may be present, if desired.

EXAMPLES

Example 1

Chemical Analysis of *Ecklonia maxima* Kelp Secondary Concentrate

A chemical analysis of the *Ecklonia maxima* secondary concentrate was made and the results of the analysis are provided in Tables 1-3 below. An LC-DAD carotenoid analysis yielded the chromatogram shown in FIG. 1. Comparisons to a standard curve indicates that fucoxanthin is present in an amount of about 3.5 µg/ml and β-carotene is present in an amount of about 0.44 µg/ml.

TABLE 1

| COMPONENTS | | INGREDIENTS | |
|---|---|---|---|
| Protein | 0.7 g/100 g | *Ecklonia maxima* seaweed (fresh material) | 33% |
| Amino acids | Very low | | |
| Carbohydrates | <1(LOQ) g/100 g | | |
| Ashes | 0.6 g | Water | 67% |
| Moisture | 99.0 g/100 g | | |
| Fat | 0.1 g/100 g | | |

TABLE 2

| GROWTH REGULATORS | | AMINO ACIDS | |
|---|---|---|---|
| AUXINS | | Alanine | 0.58 mg |
| Indole-3-acetyl-L-aspartic acid (IAAsp) | 11 mg | Valine | 0.04 mg |
| | | Glycine | 0.29 mg |
| Indole-3.acetylglycine (IAGly) | | Isoleucine | Not detected |
| Indole-3-acetyil-L-leucine (IALeu) | | Leucine | Not detected |
| | | Proline | 0.72 mg |
| Indole-3-lactic acud (ILA) | | Threonine | 0.31 mg |
| Indole-3-propionic acid (IPA) | | Serine | 0.11 mg |
| Indole-3-pyruvic acid (Ipia) | | Methionine | 0.07 mg |
| Indole-3-acetic acid (IAA) | | Hydroxyproline | ≥trace amount |
| CYTOKININS | 0.03 mg | | |
| Trans-zeatin (tZ) | | Phenylalanine | Not detected |
| Cis-zeatin (cZ) | | Aspartic Acid | Not detected |
| Trans-zeatin-O-glucoside (tZOG) | | Glutamic Acid | Not detected |
| | | Tyrosine | 1.01 mg |
| Cis-zeatin-o-glucoside (cZOG) | | Tryptophan | Not detected |
| Trans-zeatin riboside-O-glucoside (tZROG) | | Lysine | 0.04 mg |
| | | Arginine | 0.15 mg |
| Dihydrozeatin riboside (DHZR) | | Histidine | Not detected |
| Isopentenyladenine (iP) | | Cysteine | Not detected |
| Benzyladenine (BA) | | | |
| Ortho-topolin (oT) | | | |
| Meta-topolin (mT) | | | |
| Ortho-topolin-o-glucoside (oTOG) | | | |
| Meta-topolin-o-glucoside (mTOG) | | | |

TABLE 3

| MACRO/MICRO NUTRIENTS | | PHYSICAL PROPERTIES | |
|---|---|---|---|
| Nitrogen (N) | 1618 mg/kg | State | Liquid |
| Phosphorus (P) | 2932 mg/kg | Viscosity | 3.9 cps |
| Potassium (K) | 6 mg/kg | Specific gravity | 1.007 (LTM 163) |
| Sulfur (S) | 1416 mg/kg | | |
| Calcium (Ca) | 3830 mg/kg | pH | 5.5 |
| Boron (B) | 8 mg/kg | Solubility | Soluble in Water |
| Copper (Cu) | 307 mg/kg | | |
| Iron (Fe) | 628 mg/kg | Boiling point | 95° C. |
| Magnesium (Mg) | 3930 mg/kg | Receding surface tension (dynes/cm) | 63.6 |
| Manganese (Mn) | 42 mg/kg | | |
| Zinc (Zn) | 206 mg/kg | VITAMINS | |
| Lead (Pb) | 1.32 mg/kg | Vitamin A | None detected |
| Cadmium (Cd) | 0.24 mg/kg | | |
| Chromium (Cr) | 2.16 mg/kg | Vitamin E | None detected |
| Nickel (Ni) | 3.12 mg/kg | | |
| Tin (Sn) | 0.21 mg/kg | Vitamin C | 0.6 mg/100 g |
| Sodium (Na) | 12 mg/kg | | |
| Chlorine (Cl) | 11.3 mg/kg | | |

Example 2

Topical Composition of the Present Invention Formulated as a Spray Serum

The components of a topical composition of the present invention formulated as a spray serum are listed in Table 4 below.

TABLE 4

| Component | Amount (Wt %) |
|---|---|
| *Ecklonia maxima* kelp secondary concentrate | 33.3 |
| Substrate Solution (INCI name, Glucose, Arch Chemicals, Inc.) | 1.00 |
| Enzyme Solution (INCI name, Lactoperoxidase/Glucose oxidase, Arch Chemicals, Inc.) | 0.05 |
| Citric acid | 0.35 |
| Sodium citrate | 0.96 |
| Deionized water | 64.34 |
| Total | 100 |

The spray serum formulation in the form of a water-like emulsion is characterized as having a pH value of from about 4.2 to 6.5 with a water-like viscosity suitable for application as a spray.

Example 3

Formulation Process for Preparing the Topical Composition of Example 2

The topical composition of Example 2 was prepared in the amounts listed in Table 4 in a suitable mixing vessel equipped with a propeller agitator at about room temperature. The *Ecklonia maxima* kelp primary concentrate was filtered through a sieve-like material (e.g., cheesecloth) into the vessel. The propeller agitator was set at moderate mixing speed. Purified deionized water was added to the vessel while mixing to achieve a solids concentration of 33 wt %. Thereafter, citric acid was then added to the mixture and mixed until completely dissolved.

Sodium citrate USP anhydrous was then slowly added into the mixture to achieve a pH in the range of from about 4.9 to 5.1. It is noted that if the pH value of the mixture goes above 5.1, add citric acid in small amounts to adjust the pH accordingly. Correspondingly, if the pH value of the mixture goes below 4.9, add sodium citrate in small amounts to adjust the pH accordingly.

Once the desired pH was achieved, the glucose, iodide, thiocyanate component was added to the mixture and mixed for about 15 minutes. After 15 minutes of mixing, the Lactoperoxidase/Glucose oxidase component was added to the mixture and mixed for about 30 minutes until uniformity was achieved. The final pH was then measured and checked to ensure proper pH range parameters.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A topical composition comprising:
   an amount of 0.1 wt % to 99 wt % based on the total weight of said composition of a concentrate derived from *Ecklonia maxima* effective for treating skin, hair and/or nails;
   an amount of 0.001 wt % to 40 wt % based on the total weight of said composition of a shelf life enhancer;
   about 1 wt % to 2 wt % based on the total weight of said composition of a dermatologically acceptable buffer suitable to buffer the composition to a pH in the range of 4 to 6 and a dermatologically acceptable carrier, and
   optionally, a member selected from the group consisting of a cosmetically or topical pharmaceutically acceptable preservative and antibacterial;
   wherein said concentrate is obtained in the absence of chemical techniques, irradiation, or drying;
   wherein said shelf life enhancer consists essentially of an enzyme component and a substrate component;
   wherein said enzyme component comprises at least a peroxidase and at least an oxidase; and
   wherein said substrate component comprises at least glucose and at least thiocyanate, and optionally further comprises iodide.

2. The topical composition of claim 1 wherein the amount of the concentrate is in the range of from about 10 wt % to 60 wt %.

3. The topical composition of claim 1 wherein the amount of the concentrate is about 33.3 wt %.

4. The topical composition of claim 1 wherein the composition is formulated as a serum.

5. The topical composition of claim 1 wherein the amount of the shelf life enhancer is in the range of from about 0.001 wt % to 30 wt %.

6. The topical composition of claim 1 wherein the amount of the shelf life enhancer is in the range of from about 0.1 wt % to 20 wt %.

7. The topical composition of claim 1 wherein the peroxidase is lactoperoxidase.

8. The topical composition of claim 1 wherein the oxidase is glucose oxidase.

9. A topical composition comprising:
   an amount of 0.1 wt % to 99 wt % based on the total weight of said composition of a concentrate derived from *Ecklonia maxima* effective for treating skin, hair and/or nails;
   an amount of 0.001 wt % to 40 wt % based on the total weight of said composition of a shelf life enhancer; and
   about 1 wt % to 2 wt % based on the total weight of said composition of a dermatologically acceptable buffer suitable to buffer the composition to a pH in the range of 4 to 6 and a dermatologically acceptable carrier,
   wherein said concentrate is obtained in the absence of chemical techniques, irradiation, or drying;
   wherein said shelf life enhancer consists essentially of an enzyme component and a substrate component;
   wherein said enzyme component comprises at least a lactoperoxidase and at least a glucose oxidase; and
   wherein said substrate component comprises at least glucose and at least thiocyanate, and optionally further comprises iodide.

10. The topical composition of claim 9 wherein the weight ratio of substrate component to enzyme component is in the range of from about from about 5:1 to 100:1.

11. The topical composition of claim 9 wherein the weight ratio of substrate component to enzyme component is about 20:1.

12. The topical composition of claim 1 wherein the enzyme component is present in an amount of least 0.001 wt % based on the total weight of the composition.

13. The topical composition of claim 1 wherein the amount of the enzyme component is in the range of from about 0.025 wt % to 1 wt %.

14. The topical composition of claim 1 wherein the amount of the enzyme component is about 0.05 wt %.

15. The topical composition of claim 1 wherein the substrate component is present in an amount of at least 0.001 wt % based on the total weight of the composition.

16. The topical composition of claim 1 wherein the amount of substrate component is in the range of from about 0.5 wt % to 10 wt %.

17. The topical composition of claim 1 wherein the amount of substrate component is about 1.0 wt %.

18. The composition of claim 16 wherein the topical composition is in the form of a serum.

19. The topical composition of claim 9 wherein the weight ratio of substrate component to enzyme component is at least 2:1.

20. The composition of claim 1 wherein said buffer is a citrate buffer.

21. The composition of claim 19 wherein said buffer is a citrate buffer.

22. The topical composition of claim 1 wherein said concentrate has a solids content of about 33.1 wt %.

23. A method of treating skin, hair and/or nails in need of treatment, comprising topically applying an effective amount of the topical composition of claim 1 to the skin, hair and/or nails.

* * * * *